(12) United States Patent
Shoji et al.

(10) Patent No.: US 7,250,096 B2
(45) Date of Patent: Jul. 31, 2007

(54) CAPILLARY ELECTROPHORESIS APPARATUS AND METHOD

(75) Inventors: Tomohiro Shoji, Hitachinaka (JP); Masaya Kojima, Mito (JP)

(73) Assignee: Hitachi High-Technologies Corporation, Tokyo (JP)

( * ) Notice: Subject to any disclaimer, the term of this patent is extended or adjusted under 35 U.S.C. 154(b) by 691 days.

(21) Appl. No.: 10/448,187

(22) Filed: May 30, 2003

(65) Prior Publication Data

US 2004/0018638 A1  Jan. 29, 2004

(30) Foreign Application Priority Data

May 31, 2002 (JP) ............................. 2002-159156

(51) Int. Cl.
*G01N 27/26* (2006.01)
(52) U.S. Cl. ...................................... 204/451; 204/601
(58) Field of Classification Search ........ 204/451–455, 204/601–605, 401
See application file for complete search history.

(56) References Cited

U.S. PATENT DOCUMENTS 5,116,471 A   5/1992 Chien et al.

6,217,731 B1 *   4/2001 Kane et al. .................. 204/451
2002/0003091 A1   1/2002 Kojima et al.

FOREIGN PATENT DOCUMENTS

| JP | 10-206382 | 8/1998 |
|----|-----------|--------|
| JP | 11-326276 | 11/1999 |
| WO | WO 89/10550 | 11/1989 |

OTHER PUBLICATIONS

"Agilent capillary electrophoresis system", Agilent Technologies Broshure, Sep. 1, 2001, pp. 1-12.
European Search Report, dated Sep. 26, 2003.

\* cited by examiner

*Primary Examiner*—Nam Nguyen
*Assistant Examiner*—Jeffrey Barton
(74) *Attorney, Agent, or Firm*—Dickstein Shapiro LLP (57) ABSTRACT

An electrophoresis apparatus is provided in which negative effects caused by abnormalities in a current-carrying path in an electrophoresis apparatus can be avoided or reduced. The current flowing in the current-carrying path during electrophoresis can be measured to detect the state of a separating medium, and the application of a voltage to the current-carrying path can be interrupted.

7 Claims, 6 Drawing Sheets

CAPILLARY ELECTROPHORESIS APPARATUS AND METHOD

FIELD

The present teachings relate to a capillary electrophoresis apparatus for separating and analyzing samples, such as nucleic acids or proteins.

BACKGROUND

A known capillary electrophoresis apparatus is the Prism 3100, by Applied Biosystems. This apparatus can detect an electric current flowing between an electrode in a cathode-side buffer solution and a high voltage source, and an electric current flowing between an electrode in an anode-side buffer solution and ground.

SUMMARY

The present teachings provide a capillary electrophoresis apparatus that can avoid or reduce problems caused by defects in a current-carrying path.

The present teachings relate to an apparatus and method for measuring an electric current flowing in a current-carrying path during electrophoresis to detect the state of the current-carrying path. An abnormality, such as the growth of air bubbles, can be detected based on changes in the electric current in the current-carrying path. A countermeasure, such as the termination of electrophoresis, can be undertaken upon detecting an abnormality. As a result, adverse effects such as electric discharge that can be caused by continuing electrophoresis after an abnormality has occurred, can be avoided.

The present teachings relate to an apparatus and method that can measure an electric current flowing in a current-carrying path when a predetermined voltage is applied during electrophoresis for detecting the state of the current-carrying path. A determination can be made whether the current-carrying path is suitable for electrophoresis based on the detected value of the electric current when a voltage that would not cause adverse effects such as electric discharge is applied. As a result, the state of a separating medium can be easily determined, and adverse effects, such as electric discharge, can be avoided even in an abnormal situation, such as when the capillaries are not filled with a separating medium.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description herein and appended claims.

It is to be understood that both the foregoing general description and the following detailed description are exemplary and explanatory only, and are intended to provide an explanation of various embodiments of the present teachings.

DETAILED DESCRIPTION OF THE VARIOUS EMBODIMENTS

Figure 1:
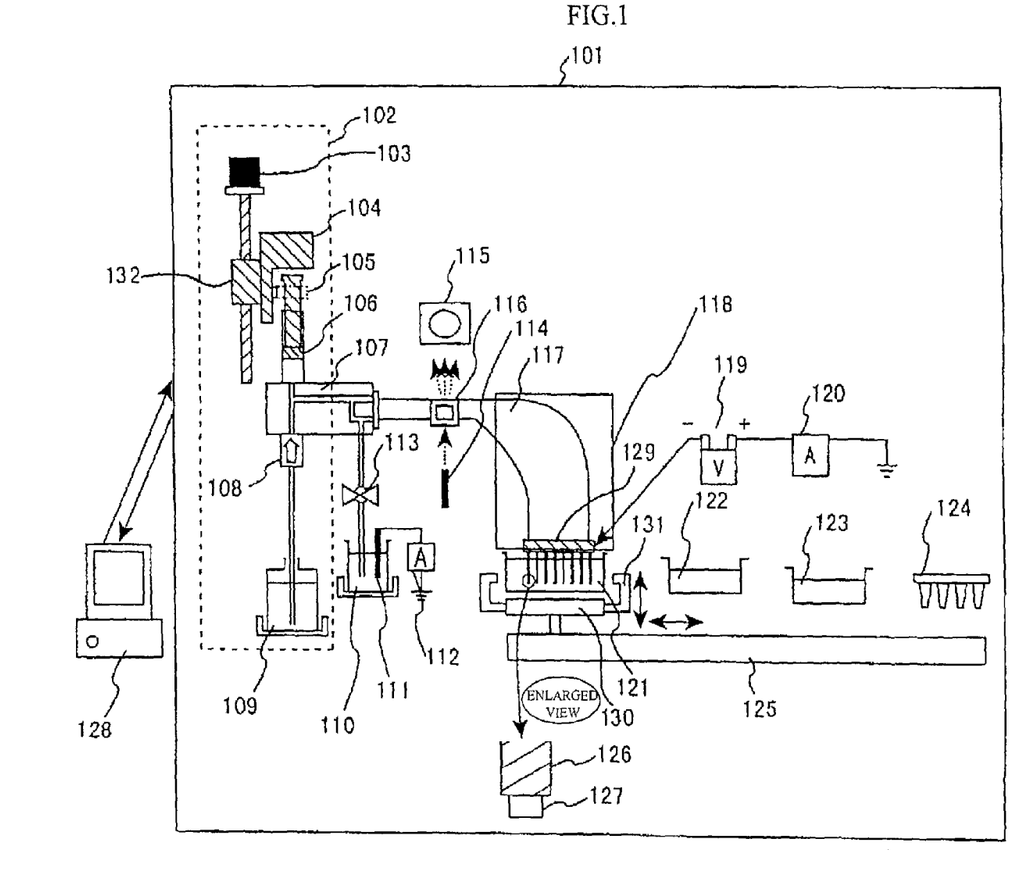
FIG. 1 schematically shows an electrophoresis apparatus according to various embodiments.

FIG. 1 schematically shows an electrophoresis apparatus according to various embodiments. The structure of the electrophoresis apparatus will be described by referring to FIG. 1.

According to various embodiments, the apparatus can include a detection cell 116 that can enable optical detection of samples, a thermostatic oven 118 that can maintain the capillaries at a constant temperature, a transporter 125 that can transport various containers to a capillary cathode end, a high-voltage power supply 119 that can apply a high voltage to the capillaries, a first ammeter 120 that can detect a current supplied by the high-voltage power supply 119, a second ammeter 112 that can detect a current flowing in an anode electrode, a capillary array 117 that can include one or more capillaries, and a pump device 102 that can inject a separation medium into the capillaries.

According to various embodiments, the capillary array 117 can be a replacable member including 96 capillaries. The capillary array 117 can include a block 129, a detection cell 116, and a capillary head. When a method of analysis is changed, the capillary array can be replaced and the lengths of the capillaries can be varied. When there is damage to or deterioration of the quality of the capillaries, the capillary array 117 can be replaced with a new one.

According to various embodiments, each capillary can be made of fused silica, for example, and can have an internal diameter ranging from 10 to several hundred microns, and can have an external diameter of at least 100 microns. The surface of the capillaries can be coated with polyimide, for example, to increase strength, except for a light-illuminable portion where the coating is not applied or has been removed. The light-illuminable portions can allow light that has been emitted by the sample migrating within the interior of the capillaries, for example, to be emitted to the exterior of the capillaries. The interior of a capillary can be filled with a separating medium to impart differences in migration speed during electrophoresis. Both a fluid and a non-fluid separating medium can be used. For example, a fluid separation medium can be implemented as the separation medium according to various embodiments.

According to various embodiments, the capillary array can, instead of including a plurality of separate capillary tubes, include a substrate such as a glass or plastic substrate having a plurality of capillary channels formed therein. The capillary channels can be formed by, for example, grooving techniques, etching techniques, masking techniques, molding techniques, chemical vapor deposition, and other manufacturing methods, or a combination thereof. Herein, the term "capillary electrophoresis" includes electrophoresis using such a substrate. When so provided, the capillary channels of the substrate can each have a respective illuminable portion that is separated, by the substrate material, from the illuminable portions of adjacent capillary channels.

According to various embodiments, the detection cell 116 can be a component for acquiring sample-dependent information. When the detection cell 116 is illuminated with excitation light, it can emit light having wavelengths that are dependent on the constituents of the sample. The light-illuminable portion and areas nearby to the 96 capillaries can be arranged and fixed to form an optically flat surface with a height tolerance of a few microns. During electrophoresis, two substantially coaxial beams of laser light can be illuminated onto the light-illuminable portions to the interior of the capillaries from both sides of the detection cell 116, such that the light can be transmitted continuously through the light-illuminable portions to the interior of the capillaries. The laser light can cause the samples migrating within the capillaries to produce light (fluorescence having sample-dependent wavelengths) that can be emitted to the exterior of the capillaries through the light-illuminable portions. The emitted light can be detected by an optical detector 115 and can be used to analyze the samples.

According to various embodiments, capillary cathode end 127 of the capillaries can be fixed through a hollow metal electrode 126 so that the tip of the capillary can protrude above the hollow electrode 126 by about 0.5 mm. The hollow electrodes 126 of the individual capillaries can be mounted on a block 129 as a single unit. The hollow electrodes 126 can be connected to a high-voltage source 119 provided in the apparatus main body, so that the hollow electrodes 126 can operate as cathode electrodes for applying voltages during electrophoresis or sample injection, for example.

According to various embodiments, filling end portions (arranged opposite to the capillary cathode ends 127) of the capillaries can be bundled by a capillary head. The capillary head is a member that can be attached and detached in a sealed manner. The capillary head can be connected to a block 107 in a pressure-tight and sealed manner. The capillaries can be filled with a fresh separation medium by a syringe 106 through the filling end portions. The separation medium in the capillaries can be replaced before each electrophoresis run to achieve improved measurement performance.

According to various embodiments, a pump device 102 can include a syringe 106 and a mechanism for pressuring the syringe 106. The block 107 can be a connecting portion for communicating the syringe 106, the capillary array 117, an anode buffer container 110, and a separation medium container 109. The pump device 102 system can be formed by an electric motor 103, a linear actuator 132, and a transport member 136 that can be adapted to have contact with the plunger of the syringe 106 for transmitting force. When the electric motor 103 is turned in a positive direction, the transport member 136 can be pressed against the plunger of the syringe 106, thereby discharging the separation medium inside the syringe 106 and injecting it into the capillaries. The transport member 136 can be provided with an electrically retractable hook 105. By turning the motor 103 in a reverse direction when the hook 105 is hooked onto the plunger, the separation medium inside the separation medium container 109 can be sucked out into the syringe 106. Positive rotation of the motor 103 is rotation of the motor in a direction in which the transport member 136 pushes the syringe, and reverse rotation is rotation in the opposite direction.

According to various embodiments, a check valve 108 can be located between the separation medium container 109 and the block 107. The valve 108 can allow the flow of separation medium from the separation medium container 109 to the block 107 while blocking the flow of the separation medium in the opposite direction. Thus, the check valve 108 can prevent the flow of separation medium back into the separation medium container 109 when injecting it into the capillary array 117.

According to various embodiments, an electric valve 113 can be adapted to open or close the flow path between the block 107 and the anode buffer container 110. The electric valve 113 can close the flow path at least when injecting separation medium into the capillaries, so that the separation medium does not flow into the anode buffer container 110. The valve can open the flow path when an electric current flows between the anode and cathode, such as during electrophoresis.

According to various embodiments, an optical detection unit can include a light source 114 for illuminating the detection cell 116, and an optical detector 115 for detecting the light emitted from the detection cell 116. When detecting samples separated by electrophoresis in the capillaries, the light-illuminable portion of the capillaries can be illuminated by the light source 114, and the emission of light from the light-illuminable portion can be detected by the optical detector 115.

According to various embodiments, the transporter 125 can include three electric motors and linear actuators for transporting containers in three axial directions, namely vertical, horizontal, and depth directions. A transport stage 130 of the transporter 125 can be capable of carrying at least one container. The transport stage 130 can be equipped with electrically-driven grips 131 by which individual containers can be held and released. The transporter 125 can transport the buffer container 121, a washing container 122, a waste-liquid container 123, and/or a sample container 124 to the cathode end of the capillaries as necessary. Additional sample containers can be stored in predetermined storage locations in the apparatus.

During operation, the main body 101 of the apparatus can be connected with a computer 128 via communication cables. An operator can have access to the data provided by the detectors in the apparatus by controlling the functions of the apparatus via the computer 128.

Figure 2:
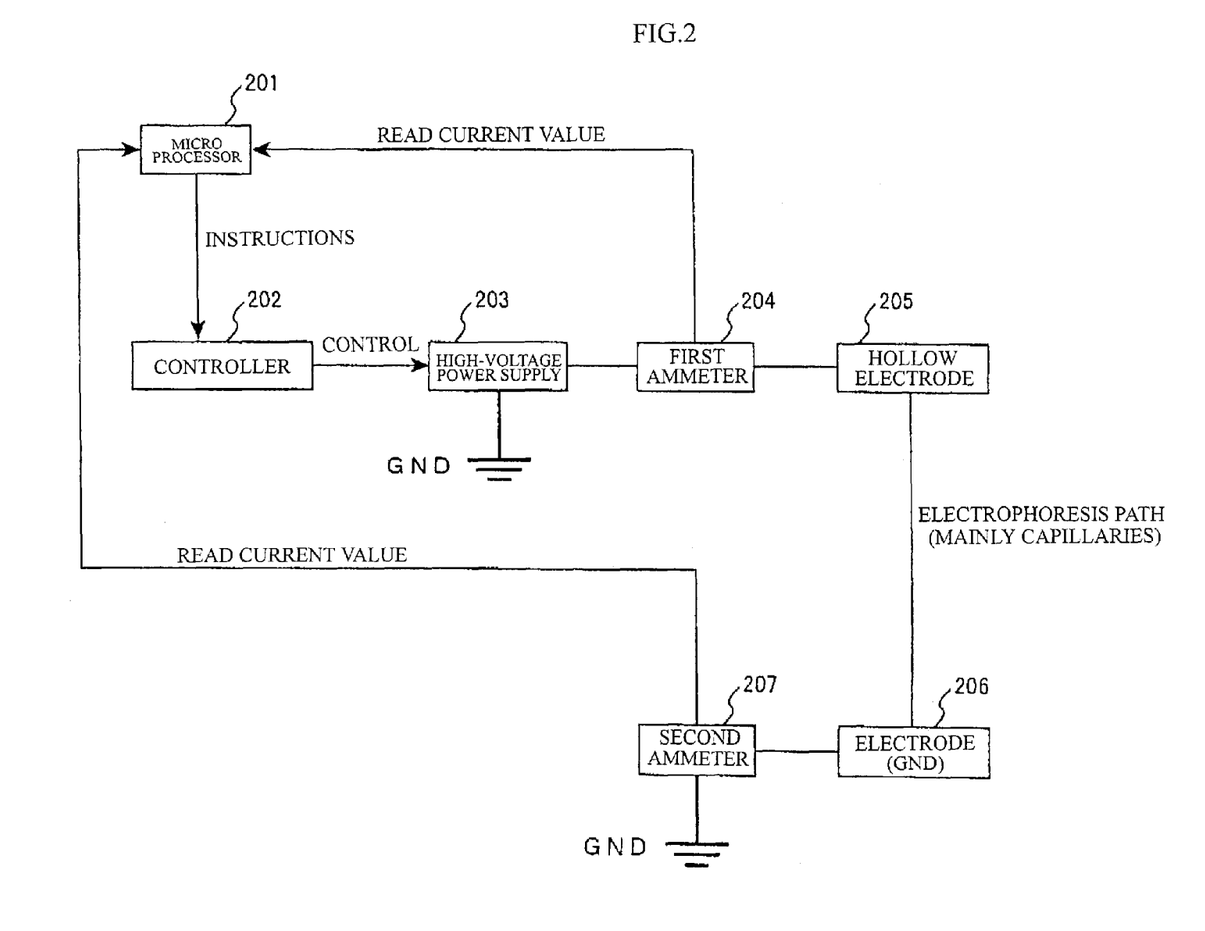
FIG. 2 is a circuit diagram of a high-voltage power supply that can constitute a voltage control device of the electrophoresis apparatus according to various embodiments.

FIG. 2 shows a circuit diagram of a voltage-control device including a high-voltage power supply for the apparatus according to various embodiments. The voltage-control device will be described by referring to FIGS. 1 and 2.

According to various embodiments, the voltage-control device can include a microprocessor 201, a controller 202, a high-voltage power supply 203, a first ammeter 204, and a second ammeter 207. The high-voltage power supply 203 can apply a voltage to a current-carrying path under the control of the controller 202. The current-carrying path can include a hollow electrode 205, a buffer solution filled in the buffer container 121, an electrophoresis path, a buffer solution filled in the anode buffer container 110, and an electrode (GND) 206. The electrophoresis path can include the separation medium filling the capillaries, the block 107, and a connection pipe (fluid pipe connecting the block 107 and the anode buffer container 110). According to various embodiments, the first ammeter can be arranged between a high voltage power supply and a hollow electrode, as shown in FIG. 2. According to various embodiments, the first ammeter can be arranged between a high voltage power supply and ground, as shown in FIG. 1.

Referring to FIG. 2 and according to various embodiments, the high-voltage power supply 203 can be in electrical connection to the hollow electrode 205 via the first ammeter 204 and to the electrode (GND) 206 via the second ammeter 207. When about 5 to about 10 kilovolts are applied across these electrodes, an electric field can be created in a direction from the hollow electrode 205 towards the electrode (GND) 206. This electric field can cause a negatively charged sample, such as nucleic acids, to move from the capillary cathode end 127 to the detection portion 116.

According to various embodiments, the first ammeter 204 can detect an electric current flowing from the high-voltage power supply 203 to the hollow electrode 205, and can transmit the value of the current to the microprocessor 201. The second ammeter 207 can detect an electric current flowing from the electrode (GND) 206 to GND, and can transmit the value of the current to the microprocessor 201. The value of the electric current and its fluctuations can be checked by the second ammeter 207, as will be described later, because the second ammeter 207 can more directly indicate the value of the current flowing in the electrophoresis path.

In the event of electric leakage, for example, between the first ammeter 204 and the second ammeter 207, the value of current indicated by the first ammeter 204 can include the value of the leaked electric current, whereas the value indicated by the second ammeter 207 does not include the leakage component. Namely, the first ammeter 204 can detect the net amount of the electric current flowing in the electrophoresis path. The interval between the first ammeter 204 and second ammeter 207 includes media, such as the buffer and separation media, with relatively large resistance compared with metals, in addition to the connecting portions, such as the block and capillaries. Thus, the interval includes a part of the circuit of FIG. 2 that is liable to experience electric leakage.

According to various embodiments, the microprocessor 201 can read electric current values from the first and second ammeters, 204 and 207, and can carry out calculations. The microprocessor 201 can then instruct the controller 202 to control the high-voltage power supply 203 into the state of either a high-voltage application, a low-voltage application, or a forced voltage shutdown. The microprocessor 201 can be capable of communicating with the externally located computer 128.

According to various embodiments, the various teachings can be used to cause a positively charged sample, such as a protein, to move from the capillary end 127 to the detection portion 116, by reversing the cathode and anode ends.

According to various embodiments, preparations for conducting electrophoresis will now be disclosed. Before initiating measurement, the operator can set up the following in the apparatus: the anode buffer container 121 holding the buffer solution; the washing container 122 holding pure water for washing the capillaries; the waste-liquid container 123 holding pure water into which the separation medium in the capillaries is to be discharged; the separation medium container 109 holding the separation medium; and the sample container 124 containing the samples to be investigated.

According to various embodiments, the anode buffer container 110 can be filled with a buffer to such a level that both the electrode (GND) 111 and the communicating tube are sufficiently submerged. The cathode buffer container 121 can be filled with the buffer to such a level that the hollow electrode 126 and the capillary cathode ends 127 are sufficiently submerged. This can be done in light of the danger of electric discharge that could occur between the high electric-potential cathode and other low electric-potential components upon the application of high voltage, if the amount of the buffer is insufficient or if the measurement is initiated with the buffer container 121 empty. It is also desirable to have the buffer levels equal, so that the separation medium in the capillaries is not moved by the pressure caused by height differences.

According to various embodiments, the flow paths utilized during electrophoresis, or the flow paths utilized for transporting the separation medium to those flow paths, can all be filled with separation medium before the measurement starts. Normally, when the apparatus is used continuously, these flow paths can be filled with separation medium. When the flow paths are refilled with separation medium after the capillary array is replaced or the flow paths are washed, the operator can refill the flow paths with separation medium by operating the pump device 102 of the apparatus or by manually operating the syringe 106.

The operator can then visually check to see if any air bubbles remain or any foreign substances are mixed in the flow paths. It is possible that air bubbles or foreign substances can remain mixed due to operational mistakes or improper checking. For example, micro-sized air bubbles can easily be missed by visual inspection. Such air bubbles or foreign substances in the flow paths could provide large resistance when the electrophoresis path is energized, possibly resulting in lowered analysis accuracy due to deficient conduction, or damage to components due to discharge. Even micro-sized air bubbles could be expanded by Joule heat during electrophoresis, eventually blocking the flow paths causing electric discharge as disclosed above. Thus, the operator should pay attention to the condition of the flow paths before starting an analysis. After setting the computer for a particular analysis to be initiated, the operator can initiate the measurement. The analysis can involve applying a high voltage to the electrophoresis path.

Figure 3:
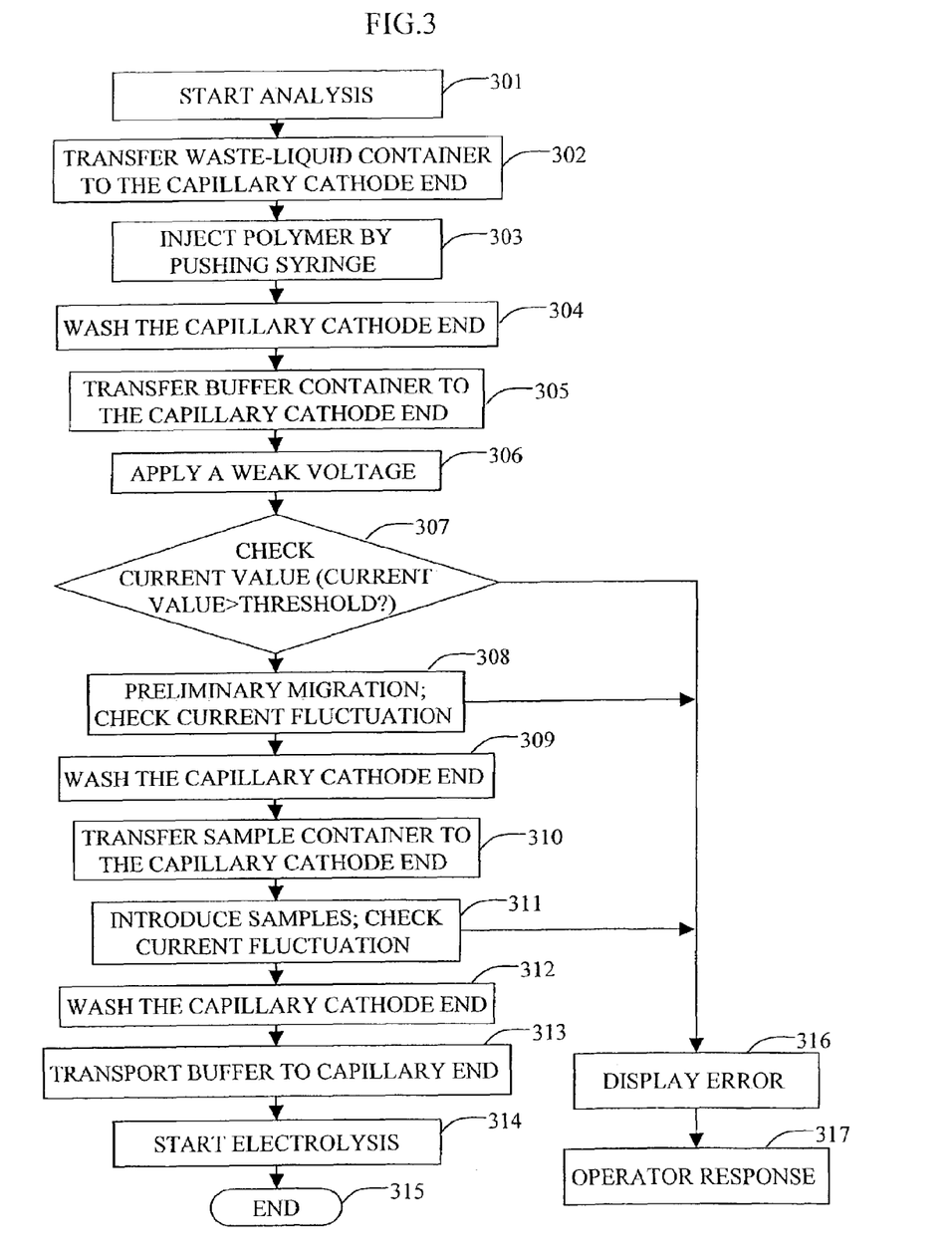
FIG. 3 shows a flowchart from the start of an analysis to the end according to various embodiments.

FIG. 3 shows a flowchart that discloses the sequence from the start of an analysis to the end of an analysis. The apparatus can initiate an analysis in response to an instruction from the computer 128 (301). First, the transporter, with which the apparatus is equipped, can transport the waste-liquid container to the capillary cathode ends in preparation for the injection of separation medium into the capillaries (302). Then, the pump device can inject a separation medium into the capillaries (303). After a predetermined amount of separation medium is injected, the transporter can transport the washing container to the capillary cathode portion, where the capillary cathode ends can be submerged and washed in the pure water in the washing container (304). The transporter can then transport the buffer container to the capillary cathode portion (305). Then, the condition of the current-carrying path can be confirmed (by confirming the value of the electric current upon application of a low voltage).

According to various embodiments, confirmation of the condition of the current-carrying path can include a sequence including the application of a weak voltage (306), the checking of the current value (307), the displaying of errors (316), and a response by the operator (317). By this sequence, abnormalities such as, for example, a shortage of buffer solution, air bubbles remaining in the electrophoresis path, or the mixing in of dust can be identified. As a result, the danger of creating electric discharge in the electrophoresis path by the application of high voltage when there is a mistake made in the pre-preparation stage can be avoided.

According to various embodiments, in the step of applying a weak voltage (306), a voltage can be applied that is lower than that applied during preliminary electrophoresis (308), sample introduction (311), and electrophoresis (313). The magnitude of the voltage can be such that no electric discharge is created, even if an abnormality, such as a shortage of buffer solution, air bubbles remaining in the electrophoresis path, or the mixing of dust, has occurred. According to various embodiments, a voltage of about 1 kilovolt can be applied and the value of the electric current can be confirmed about three seconds later. This can take place to obtain an accurate current value commensurate with the voltage, in consideration of the rise time of the electric current. A wait time of about a few seconds can be sufficient. The value that is detected can then be read from the second ammeter 207 on the anode side.

During the electric current check (307), the value of the electric current detected by the weak voltage application (306) can be compared with a threshold. The threshold can be determined in view of parameters that can influence the value of the electric current, such as the kind of application, the specific length and number of the capillaries, and the kind of separation medium used. Electric current values that can be obtained under various use conditions can be experimentally investigated, and a value that is about half or one-third of each of those current values can be used as the threshold. If the value of the electric current is smaller than the threshold, an abnormal state or current-inhibiting factors, such as a shortage of buffer solution or the presence of air bubbles in the electrophoresis path, can be assumed. As a result, an error can be presumed to exist in the electrophoresis path. If such an abnormality is recognized, the voltage can be shut down immediately to prevent damage to the components by way of an electric discharge.

According to various embodiments, an error message can be displayed on the display of the control computer (316), and a response by the operator can be demanded (317). Recognizing the error, the operator can visually inspect the electrophoresis path for any air bubbles or a mixing of a foreign substance. If an abnormality is identified, a countermeasure can be planned, and either the analysis can be resumed or maintenance by service personnel can be requested. For example, if the cause of the abnormality turns out to be air bubbles or the mixing of a foreign substance, the interior of the flow path can be refreshed by the pump device 102, or by manually operating the syringe 106. The comparison of current values and the decision concerning any abnormality can be carried out by software. The threshold used for the decision concerning any abnormality can be stored in software.

According to various embodiments, confirmation of the condition of the current-carrying path can be implemented prior to sample introduction (311) and electrophoresis (314). As a result, mistakes in the initial preparation step can be avoided, such as a shortage of the buffer volume resulting in the buffer solution failing to contact the electrode, or the mixing of relatively large air bubbles in the electrophoresis path causing a failure in establishing electric conduction.

According to various embodiments, if there is no abnormality in the current-carrying path, a predetermined voltage can be applied and a preliminary migration can be initiated (308). The preliminary migration can be performed to optimize the condition of the separation medium in the capillaries for analysis prior to the main analysis process from sample introduction to electrophoresis. During preliminary migration, a voltage of about 10 kilovolts or more can be applied for about 2 or more minutes. After preliminary migration, the capillary cathode ends can be washed again in the washing container (309), and the sample container 124 can be transported to the capillary cathode ends. When a voltage in the order of about several kilovolts is applied to the capillary cathode electrode in the sample solution contained in the sample container 124, an electric field can be created between the sample solution and the anode electrode. This electric field can cause the samples in the sample solution to be introduced into the capillaries (311).

After the sample is introduced, the capillary cathode ends can be washed in the washing container (312), and then the buffer container can again be transported to the capillary cathode end (313). A predetermined voltage can then be applied to start electrophoresis (314).

According to various embodiments, electrophoresis (314) is the process of providing the samples in the capillaries with mobility by the action of an electric field created between the cathode and anode buffers, so that the samples can be separated by differences in mobility depending on their characteristics. The separated samples can be optically detected sequentially in the order of their arrival at the detector. For example, when the samples are DNA, differences in mobility can be caused by their individual base lengths, so that DNA with a shorter base length can move faster and can pass the detector first. The detection of DNA by the detector is made possible by attaching a fluorescent dye to it. Normally, the measurement time and the voltage-applied time can be set to accommodate a sample with the longest migration time.

According to various embodiments, once a predetermined time has passed after the application of voltage, and desired data has been obtained, the application of voltage can be terminated to bring electrophoresis to an end (315).

In each of the above-described sequences of preliminary migration (308), sample introduction (311), and electrophoresis (314), a process of detecting abnormalities in the electrophoresis path by monitoring electric current fluctuations can be carried out. In these three sequences, a high voltage of about 2 kilovolts or more can be applied to the electrophoresis path. If, for example, the application of a high voltage is maintained while micro-sized air bubbles (that cannot be detected by the earlier condition confirmation by a weak voltage) remain in the electrophoresis path, the air bubbles can grow as the temperature inside the flow path rises. When the current-carrying path is blocked by the expanding air bubbles, an electric discharge can be caused. For at least this reason, an apparatus can be equipped with the ability to detect abnormalities in the electrophoresis path while a voltage is applied.

Figure 4:
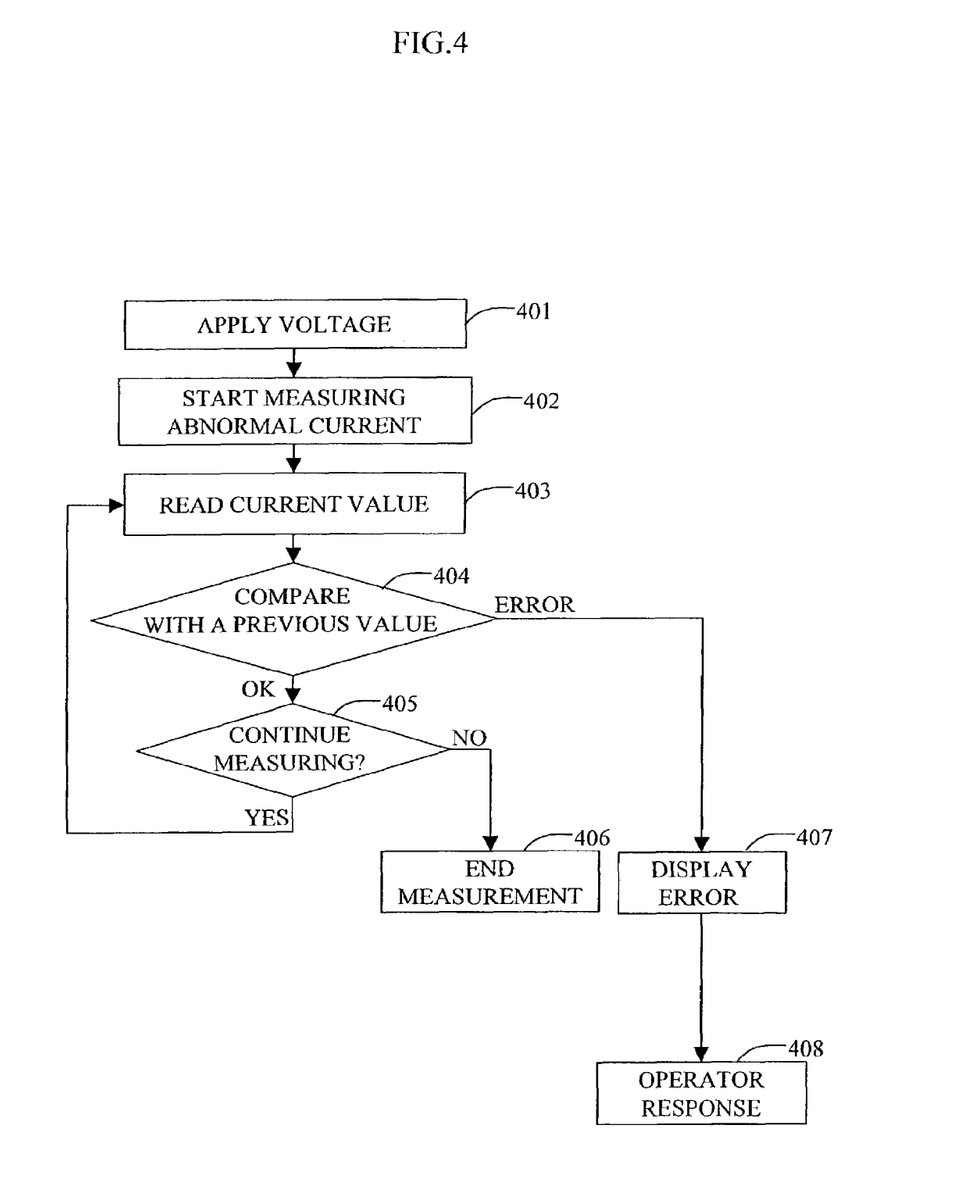
FIG. 4 shows a flowchart for detecting abnormalities in an electrophoresis path according to various embodiments.

FIG. 4 shows a flowchart for a process of detecting abnormalities in the electrophoresis path. A method of detecting abnormalities in the electrophoresis path by monitoring current value fluctuations will be described by referring to FIG. 4.

First, a voltage can be applied, and the sequence of either preliminary migration, sample introduction, or electrophoresis can be initiated (401). This can be followed by measuring abnormal currents, and, if an abnormality is detected in the electrophoresis path, the abnormal current measuring function can be placed into operation (402). The value of electric current can then be obtained from the second ammeter 207 (403). If there is a current value that has been acquired in the past, it can be compared with the latest current value to determine the condition of the current-carrying path (404). The value of the electric current is stable value when the current-carrying path is normal, and any fluctuations are gradual. On the other hand, if the electrophoresis path is blocked by air bubbles, for example, the electric current would fluctuate suddenly. Accordingly, by monitoring the degree of fluctuation in the electric current, and specifically, the gradient of the electric current, abnormalities in the electrophoresis path can be instantly detected while the voltage is applied. A determination that there is an abnormality in the current-carrying path can be made when the amount of decrease in the current value per unit time has exceeded the threshold. This decision technique will be described in detail below.

According to various embodiments, when an abnormality is detected in the current-carrying path, the voltage can be terminated and the measurement can be stopped to prevent electric discharge. An error can then be displayed (407), and a response by the operator can be demanded (408). The operator, recognizing the error, can then visually inspect the electrophoresis path for any air bubbles or foreign substances. If an abnormality is found, a countermeasure can be taken, and either the analysis can be resumed or maintenance by service personnel can be requested. For example, if the cause of the abnormality is air bubbles or the mixing of a foreign substance, the flow path can be refreshed by the pump device 102, or by manually operating the syringe 106. If no abnormality is found at step (404), either the application of voltage can be maintained or confirmed (405). When the voltage is to be cut off, the monitoring of the electric current fluctuations can be stopped before cutting off. If the application of voltage is to be continued, the sequence from the electric current value reading step (403) to step (405) can be repeated.

Figure 5:
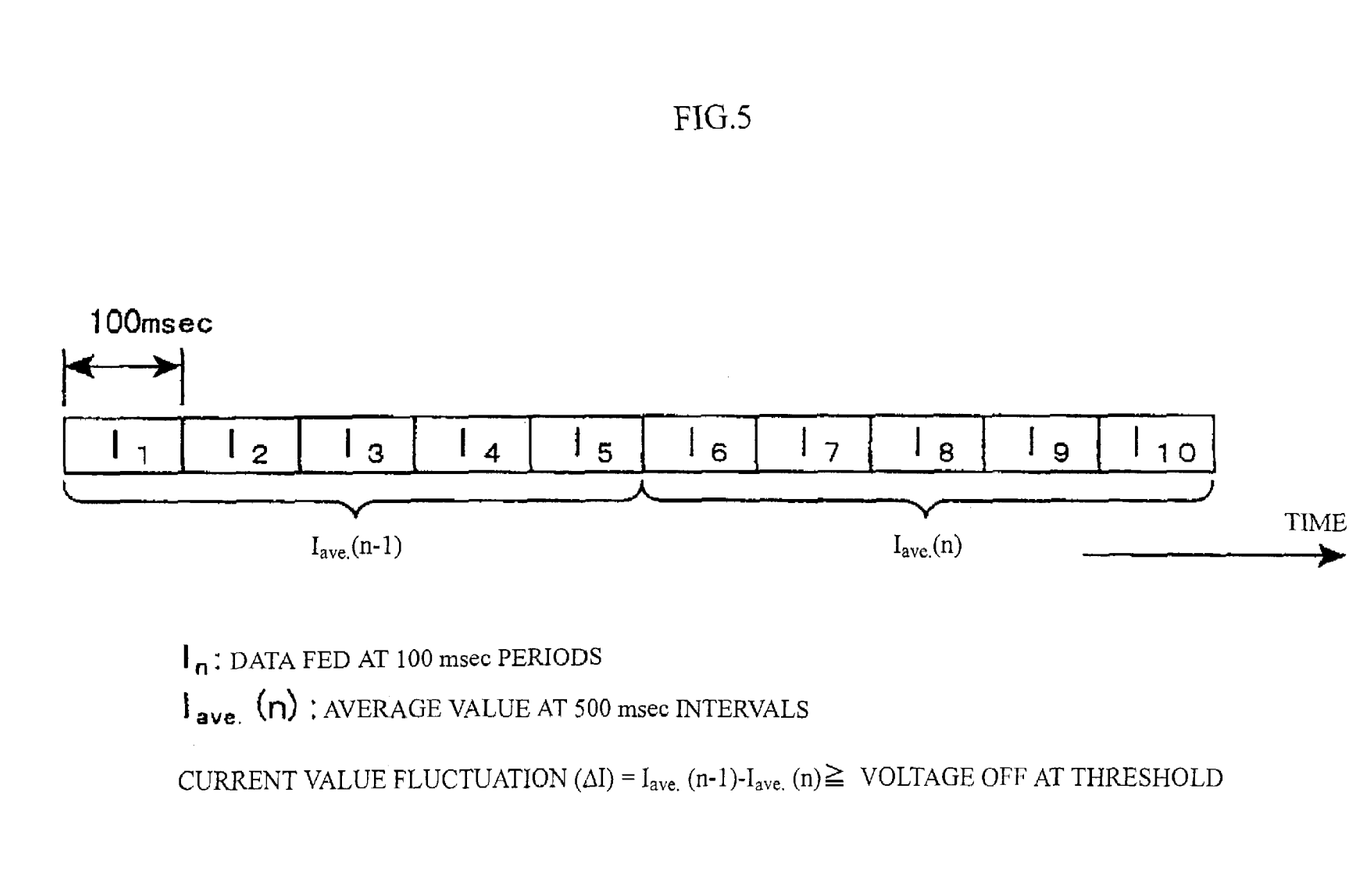
FIG. 5 shows a method of detecting and comparing electric current fluctuations according to various embodiments.

FIG. 5 schematically illustrates a method of detecting and comparing electric current fluctuations, and corresponds to the "COMPARE WITH A PREVIOUS VALUE" step of FIG. 4. The method of judging the condition of the migration path based on an average value of the electric current will be described by referring to FIG. 5.

While the obtained electric current values may be compared as they are in step (404), an average can be taken over a certain time period and then compared, according to various embodiments. This operation has the effect of smoothing the electric current values over a certain period, so that minute fluctuations in the electric current values due to detection accuracy or the influence of sporadically generated static noise can be reduced.

According to various embodiments, while voltage is being applied, the microprocessor 201 can read the electric current value fluctuations at periods of about 100 msec, and can check them. The electric current values that are read can be sequentially recorded while they are designated as $I_1$, $I_2$, $I_3$, . . . and so on, up to $I_{10}$, in chronological order. Thereafter, the latest five values, namely $I_6$ to $I_{10}$, can be averaged. The previous five values, namely $I_1$ to $I_5$, can also be averaged. As a result, each of the resultant average values can indicate the average value for a 500-msec interval when the electric current values have been read at 100 msec periods. The difference between the average value ($I_{ave}.(n)$) in the latest 500-msec interval and the average value ($I_{ave}.(n-1)$) of the previous 500-msec interval can be defined as a fluctuation ($\Delta I$) of the electric current value (I).

In a normal state, the electric current value (I) can assume a stable value and, therefore, its fluctuation $\Delta I$ can be almost zero. However, if the air bubbles in the flow path grow due to the heat produced by the electric current and they block the flow path, as mentioned above, the electric current value (I) can suddenly decrease and its fluctuation value $\Delta I$ can rise. As a result, a certain threshold can be set, and the voltage can be removed from the electrophoresis path immediately after the electric current value fluctuation has exceeded the threshold. The threshold can be of such a magnitude that it is not observed in a normal state but can be easily exceeded when an abnormality, such as the blocking of the flow path by air bubbles, is produced in the electrophoresis path. This kind of desirable threshold can be set, for the fluctuation ($\Delta I$) of the electric current value due to detection accuracy in a normal state is far smaller than that during the occurrence of an abnormality. While the difference between $I(n)$ and $I(n-1)$ can be defined as the fluctuation of the electric current value, the fluctuation of the electric current value can be determined based on the ratio of $I(n)$ and $I(n-1)$.

According to various embodiments, it is also possible to detect abnormalities in the electrophoresis path based on the variation of the electric current value. For example, a threshold can be established based on an expected value of the electric current in the event of the growth of air bubbles in the electrophoresis path. The electric current value can be continually compared with the threshold, and electrophoresis can be terminated if the electric current value drops below the threshold, thereby indicating that the flow path is blocked by air bubbles.

Figure 6:
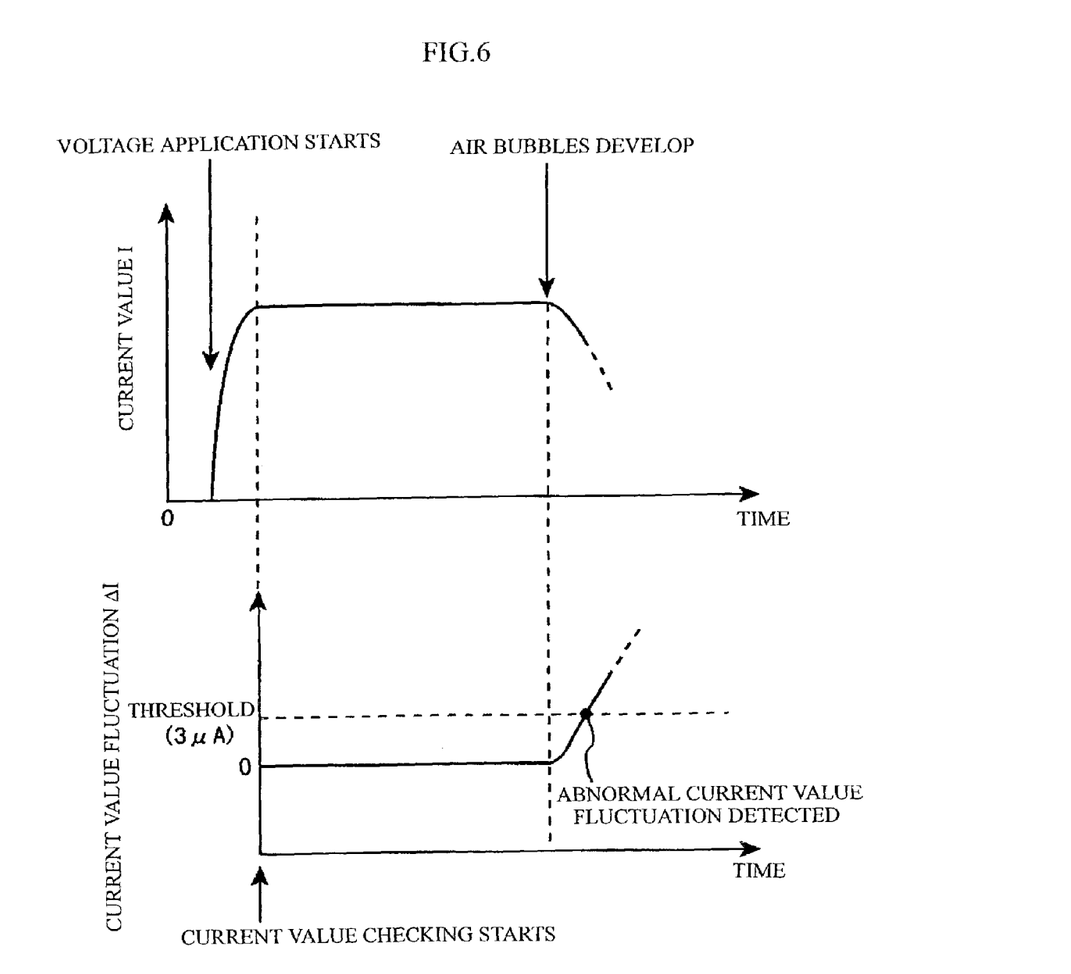
FIG. 6 graphically illustrates electric current changes and fluctuations according to various embodiments.

FIG. 6 shows electric current fluctuation and its detection, showing functional changes from the start of measurement to the detection of an abnormality. Hereafter, the changes in the actual current value (I) and its fluctuation ($\Delta I$) will be described. The top of FIG. 6 shows the time elapsed on the horizontal axis, and the electric current value on the vertical axis. FIG. 6 plots changes in electric current as a voltage is applied at a point and the electric current can then enter a stable state. This can be followed by the expansion of the air bubbles as the temperature in the flow path increases and the air bubbles blocking the flow path at another point. The bottom of FIG. 6 shows the time elapsed on the horizontal axis and the fluctuation of the electric current as obtained by the method described by referring to FIG. 5. The bottom of the figure shows the fluctuation of the current value from the time when the current value has entered the steady state, until the time when the flow path is blocked by air bubbles.

As shown in the top of FIG. 6, when a voltage is applied, an electric current can flow that is commensurate with the applied voltage. In operation, the electric current can be stabilized not long after the application of a voltage if there are no abnormalities in the electrophoresis path. The electric current value (I) can be stabilized even if minute air bubbles are mixed in the electrophoresis path if they do not block the flow path. As the air bubbles grow in size due to heating by applying an electric current great enough such that the air bubbles block the electrophoresis path, the electric current value (I) can greatly decrease. Such a drastic reduction in electric current can also be caused by an accident, such as short-circuiting in the high-voltage source, or by breakage in the electrophoresis path by an insulator.

According to various embodiments, the electric current fluctuation caused by the above electric current changes is shown at the bottom of FIG. 6. While the electric current value (I) is in a stable period, the fluctuation ($\Delta I$) can be nearly zero. Once the electric current value (I) drops due to the growth of air bubbles, the electric current fluctuation ($\Delta I$) can increase and when it reaches the set threshold, an abnormal fluctuation in electric current value can be detected.

In a system where normally an electric current of several hundred amperes flows, abnormalities in the electrophoresis path, such as the growth of air bubbles, can be detected by the above-described method by setting the threshold at several microamperes.

According to various embodiments, when the voltage value is changed during the application of voltage, the electric current can simultaneously change, and this could result in operational failure. Specifically, the function could make a false detection. In order to prevent this, a method can be employed whereby the abnormal electric current detection function is terminated before the voltage is changed, and then resumed once the electric current has entered a stable region.

According to various embodiments, another method can be employed when the voltage is changed in an increasing direction. Specifically, electric current fluctuation in an increasing direction can be ignored and fluctuations in a decreasing direction can be monitored, based on the fact that electric current decreases when air bubbles are produced. In this case, even if the timing of the application of voltage and that of the detection of abnormal fluctuation are reversed Δ that is, even if the voltage is applied after the detection of abnormal fluctuation Δ there is no possibihty of false detection.

The method of detecting abnormalities in the electrophoresis path based on values of electric current and its fluctuation, according to various embodiments, can be applied to systems that are susceptible to damage by abnormalities, such as air bubbles, in the electrophoresis path. These include systems that employ a non-fluid separating medium, or systems in which the separating medium in the capillaries is not replaced for each analysis.

Those skilled in the art can appreciate from the foregoing description that the present teachings can be implemented in a variety of forms. Therefore, while these teachings have been described in connection with particular embodiments and examples thereof, the true scope of the present teachings should not be so limited. Various changes and modifications may be made without departing from the scope of the teachings herein.

What is claimed is:

1. A method of performing electrophoresis utilizing a capillary, the method comprising:
   filling the capillary with a separating medium;
   applying a voltage to a current-carrying path including the separating medium prior to performing electrophoresis, the applied voltage being smaller than a voltage that is applied during electrophoresis;
   detecting a first value of the electric current flowing in the current-carrying path;
   determining a state of the current-carrying path based on the first value of the electric current that is detected;
   performing electrophoresis while detecting a second value of the electric current flowing in the separating medium after determining that a state of the current-carrying path is suitable for electrophoresis; and
   terminating performing electrophoresis based on the detected second value of the electric current,
   wherein electrophoresis is terminated when a rate of change of the detected second value of the electric current has exceeded a predetermined value.

2. The electrophoresis method of claim 1, wherein the state that the current-carrying path is not suitable for electrophoresis is determined when the first value of the electric current that is detected is smaller than a predetermined value.

3. The electrophoresis method of claim 1, wherein the voltage that is applied to the current-carrying path is smaller than a voltage that produces electric discharge when the capillary is not filled with the separating medium, or when a buffer-solution container forming part of the current-carrying path does not contain an appropriate amount of a buffer solution.

4. The electrophoresis method of claim 1, wherein the predetermined value is determined based on at least one of a length of a capillary, the number of capillaries, the separating medium, and the method of measurement.

5. A method of performing electrophoresis utilizing a capillary, the method comprising:
   filling the capillary with a separating medium;
   applying a voltage to a current-carrying path including the separating medium prior to performing electrophoresis, the applied voltage being smaller than a voltage that is applied during electrophoresis;
   detecting a first value of the electric current flowing in the current-carrying path;
   determining a state of the current-carrying path based on the first value of the electric current that is detected;
   performing electrophoresis while detecting a second value of the electric current flowing in the separating medium after determining that a state of the current-carrying path is suitable for electrophoresis; and
   terminating performing electrophoresis based on the detected second value of the electric current,
   wherein detecting a second value of an electric current includes calculating an average value of the electric current over a predetermined period of time, and
   wherein electrophoresis is terminated when the rate of change of the average value of the electric current exceeds a predetermined value.

6. The electrophoresis method of claim 5, wherein the state that the current-carrying path is not suitable for electrophoresis is determined when the first value of the electric current that is detected is smaller than a predetermined value.

7. The electrophoresis method of claim 5, wherein the voltage that is applied to the current-carrying path is smaller than a voltage that produces electric discharge when the capillary is not filled with the separating medium, or when a buffer-solution container forming part of the current-carrying path does not contain an appropriate amount of a buffer solution.

* * * * *